United States Patent [19]

Leary et al.

[11] Patent Number: 5,024,234
[45] Date of Patent: Jun. 18, 1991

[54] ULTRASONIC IMAGING CATHETER WITH GUIDEWIRE CHANNEL

[75] Inventors: James J. Leary, Sunnyvale; John R. McKenzie, San Francisco, both of Calif.

[73] Assignee: Cardiovascular Imaging Systems, Inc., Sunnyvale, Calif.

[21] Appl. No.: 422,935

[22] Filed: Oct. 17, 1989

[51] Int. Cl.⁵ .................................................. A61B 8/14
[52] U.S. Cl. .......................... 128/663.01; 128/662.06
[58] Field of Search .................... 128/657, 658, 662.06, 128/663.01, 772; 604/22, 160, 161, 164, 264, 280

[56] References Cited

U.S. PATENT DOCUMENTS

| | | | |
|---|---|---|---|
| 4,402,684 | 9/1983 | Jessup | 604/264 |
| 4,748,982 | 6/1988 | Horzewski et al. | 128/344 |
| 4,762,129 | 8/1988 | Bonzel | 128/344 |
| 4,794,931 | 1/1989 | Yock | 128/660.03 |
| 4,821,731 | 4/1989 | Martinelli et al. | 128/662.06 |

OTHER PUBLICATIONS

Medi-Tech, Incorporated, "Ultrasound Imaging Catheter", Cat. No. 01-118, Aug. 1989.
"Announcing the Family of 2.5 mm Laserprobes" dated Dec., 1987.
Intravascular Ultrasound, edited by Bom and Roelandt, Kluwer Academic Publishers, p. 148, 1989.

Primary Examiner—Kyle L. Howell
Assistant Examiner—Kevin Pontius
Attorney, Agent, or Firm—Townsend and Townsend

[57] ABSTRACT

Intravascular catheters including both a flexible catheter body and a less flexible housing mounted at a distal end of the catheter body are provided with a flexible distal tip, preferably having a conical geometry. Guidewire channel or lumen is formed within the tip, and optionally additional guidewire lumens are formed in the housing or the distal end of the catheter body, or both. The catheters may thus be inserted and withdrawn over a guidewire without the need for the entire length of the catheter to pass over the guidewire.

7 Claims, 3 Drawing Sheets

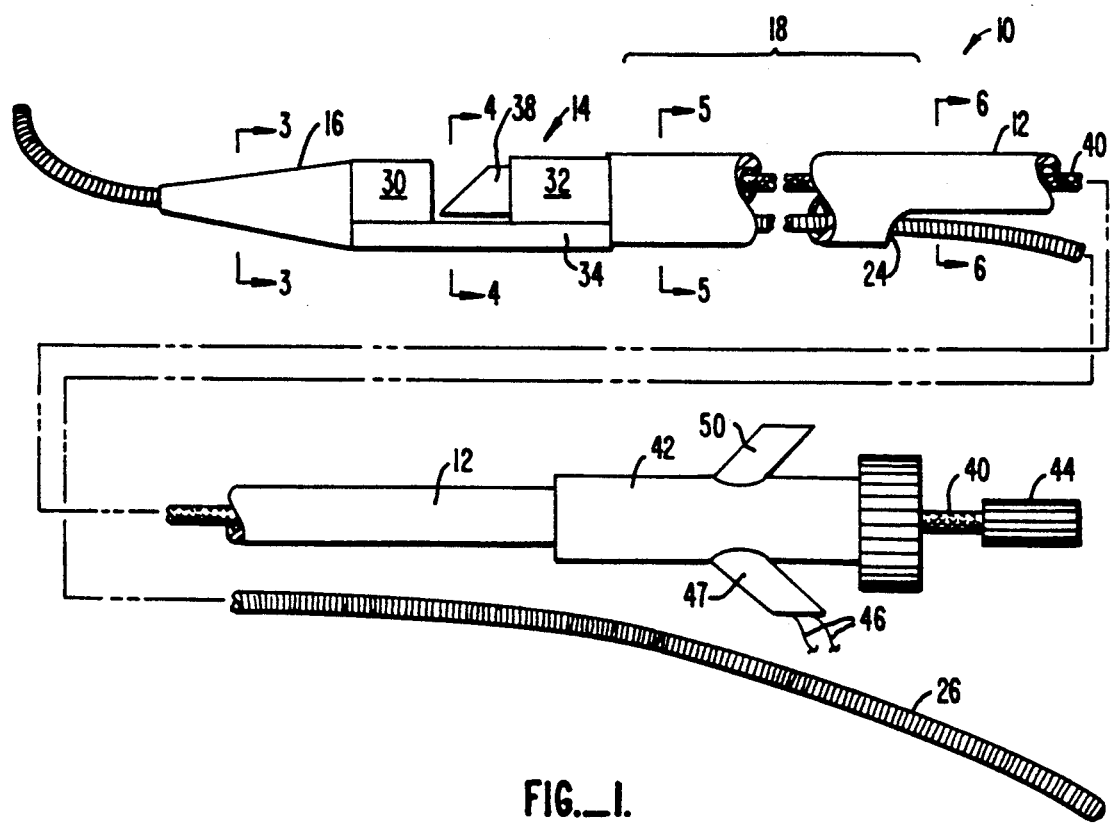
FIG._1.
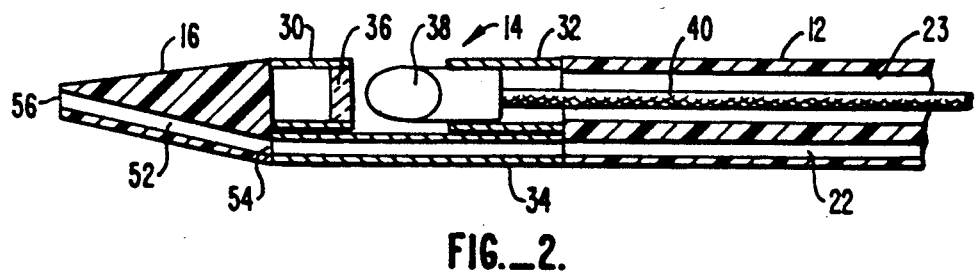
FIG._2.
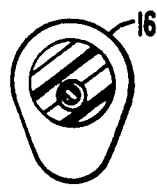
FIG._3.
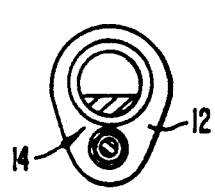
FIG._4.
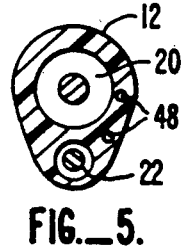
FIG._5.
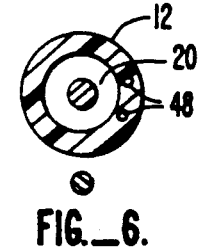
FIG._6.

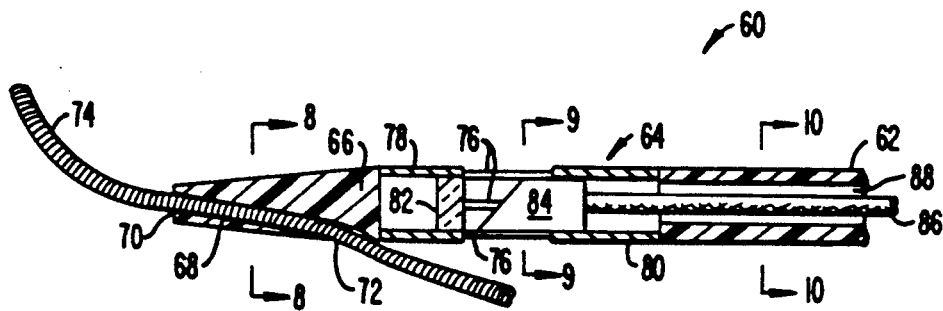
FIG._7.
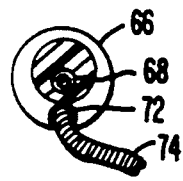
FIG._8.
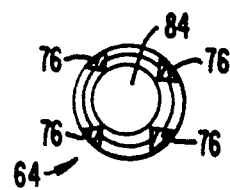
FIG._9.
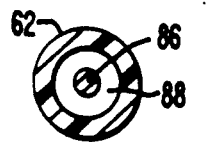
FIG._10.
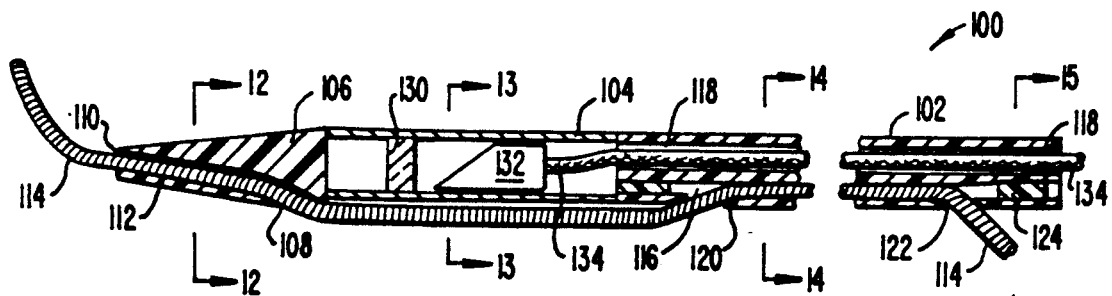
FIG._11.
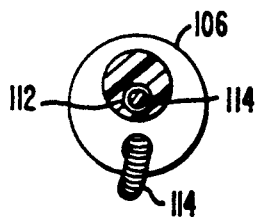
FIG._12.
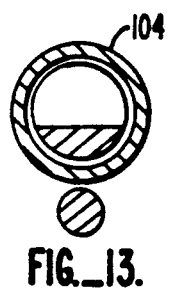
FIG._13.
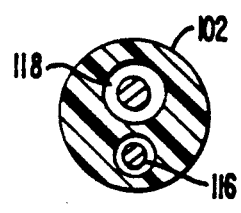
FIG._14.
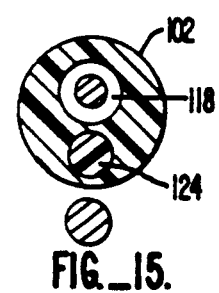
FIG._15.

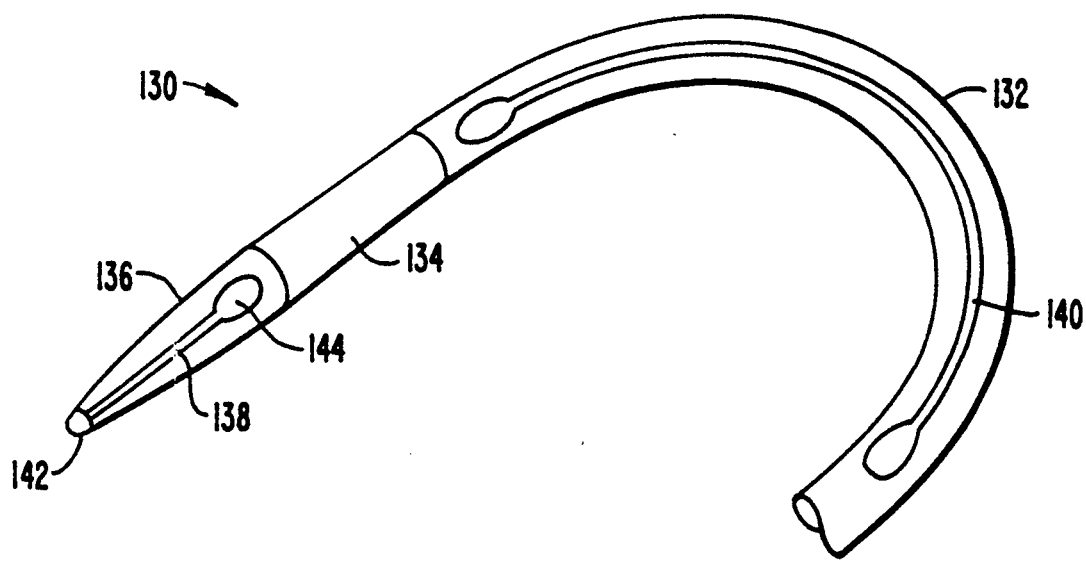
FIG._16.

ULTRASONIC IMAGING CATHETER WITH GUIDEWIRE CHANNEL

BACKGROUND OF THE INVENTION

Field of the Invention

The present invention relates generally to the construction of intravascular catheters. More particularly, the invention relates to intravascular catheters having guidewire receptacles which are compatible with distal housings having internal components therein.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs of the body and coronary blood vessels which feed the heart. When deposits accumulate in localized regions of a blood vessel, blood flow is restricted and the person's health is at serious risk.

Numerous approaches for reducing and removing such vascular deposits have been proposed, including balloon angioplasty where a balloon-tipped catheter is used to dilatate a region of atheroma, atherectomy where a blade or other cutting element is used to sever and remove the atheroma, and laser angioplasty where laser energy is used to ablate at least a portion of the atheroma. In addition to such therapeutic approaches, a variety of techniques for transluminal imaging of atheroma and other diseased regions of a blood vessel have been proposed, including endoscopic imaging techniques and ultrasonic imaging techniques. Common to all such techniques is the use of an intravascular catheter which is positioned at a desired location within the blood vessel to be treated or imaged.

Two alternative approaches may generally be employed to achieve such positioning. In the first approach, the vascular catheter is provided with a "fixed guidewire" secured to its distal end. The fixed guidewire is typically a coiled spring or other elongate resilient member having a preformed, curved tip. The catheter can then be guided through branches within the vascular network by rotating the entire catheter, causing the tip of the guidewire to enter a desired branch as the catheter is moved forward. In the second technique, entirely separate "movable guidewire" is employed. The movable guidewire is itself a coiled spring or other resilient elongate member and will generally include a curved tip similar to that provided on the fixed guidewires described above. The vascular catheter being positioned includes a guidewire lumen which generally extends down the center of the entire length of the catheter and is sized to receive the movable guidewire. The movable guidewire is first positioned within the vascular system so that its distal end extends beyond the region of interest, and the intravascular catheter is then inserted over the movable guidewire using the guidewire lumen. Such procedures using movable guidewires are commonly referred to as "over-the-wire" insertional techniques.

The use of movable guidewires enjoys a number of advantages over the use of fixed guidewires. In particular, a movable guidewire allows positioning of relatively large diameter catheters which would be difficult to manipulate using a fixed guidewire. The presence of a movable guidewire also facilitates repositioning of the catheter during use and simplifies withdrawal of the catheter and replacement by either the same catheter or a different catheter.

The use of movable guidewires with certain types of intravascular catheters, however, is problematic. Many catheters have internal components within their distal end for imaging or interventional purposes, and such components can interfere with passage of the movable guidewire through the catheter. The use of movable guidewires has been particularly troublesome with imaging catheters of the type employing ultrasonic elements at their distal end, frequently in combination with rotating mirrors. It is undesirable to penetrate the ultrasonic element thus rendering passage of a movable guidewire through the center of the catheter undesirable. Thus, such catheters have normally employed fixed guidewires at their distal ends.

A second consideration in employing movable guidewires relates to their length. In many catheters, the movable guidewire is received in a lumen which extends the entire length of the catheter body. In order to both insert the catheter and remove the catheter while leaving the movable guidewire in place, it is necessary that the movable guidewire have a length equal to at least twice that of the catheter body. In this way, the proximal end of the guidewire may be held in place at all times while the catheter is being inserted or withdrawn. The use of such long guidewires, however, proved highly inconvenient, requiring manipulation of the guidewire in the catheter at great distances from the patient. To overcome these problems, "monorail" systems have been devised for certain types of catheters, including balloon-tipped catheters and laser hot tip catheters.

In such monorail designs, the guidewire lumen extends through only a very short wire lumen formed at the distal end of the catheter. Thus, the length of the guidewire can be reduced to a length which need only be equal to the length of the catheter plus the short length of the wire lumen at the distal end. Such monorail guidewire lumens, however, have not generally been employed in catheters having mechanical and electrical components in their distal end, such as ultrasonic imaging catheters where the passage of a guidewire, even for a short length, is problematic.

For these reasons, it would be desirable to provide intravascular catheters having alternative receptacle constructions for receiving movable guidewires. It would be particular desirable to provide such intravascular catheters with receptacles for receiving movable guidewires in such a way that interference with the internal components is minimized. Preferably, such guidewire receptacles should provide for monorail operation which facilitates separation of the catheter from the guidewire as the catheter is withdrawn.

Description of the Background Art

U.S. Pat. No. 4,794,931, describes a vascular ultrasonic imaging catheter employing a rotating mirror or ultrasonic element to produce a two-dimensional image. The catheter is illustrated to include a fixed guidewire at its distal tip. U.S. Pat. No. 4,762,129, illustrates a balloon dilatation catheter having a laterally-offset lumen extending axially through the balloon and capable of receiving a movable guidewire. U.S. Pat. No. 4,748,982, discloses a balloon dilatation catheter having parallel lumens extending through the catheter body. A side port opens to one of said lumens proximally of the balloon, allowing a movable guidewire to extend from said side port the entire distance to the distal tip of the catheter. Trimedyne, Inc. of Tustin, Calif., sells a hot tip laser catheter having an enlarged metal tip with an axially-offset lumen for receiving a guidewire. The catheter is described in a brochure entitled "*Announcing the family of 2.5 mm Laserprobes*" dated December 1987.

SUMMARY OF THE INVENTION

According to the present invention, an intravascular catheter comprises a flexible catheter body having proximal and distal ends with a housing secured to the distal end. A flexible tip is secured to a distal end of the housing, and a guidewire channel is formed in the tip, extending from a first port on its proximal periphery to a second port at the distal end of the tip. Usually, the flexible tip has a conical geometry, where the first port is formed adjacent the base and the second port is formed at the conical apex. By providing a guidewire port at the periphery of the flexible tip, the guidewire can be partially or entirely bypassed around the housing in order to minimize the design impact on the internal components within the housing. Such design is particularly useful for ultrasonic imaging catheters having ultrasonic imaging components within the housing. Bypassing the guidewire around the housing can minimize the diameter of the catheter, improving access to small blood vessels and tight atherosclerotic lesions and minimizing the image artifact resulting from the guidewire.

In a first exemplary embodiment, both the housing and the catheter body are provided with radially-offset guidewire channels which are generally aligned with the first peripheral port on the flexible catheter tip. The channel in the housing usually extends the entire length and is typically formed as a separate tube adjacent to the portion of the housing which encloses the internal components. The guidewire channel on the catheter body, however, will extend only a portion of the body length where a peripheral access port is provided. In this way, the guidewire will be received in a radially-offset guidewire channel which extends from a peripheral port on the catheter body to an apical port on the flexible catheter tip. Such constructions provide a very high degree of maneuverability and facilitate pushing the catheter through small, tortuous paths where the tendency for the guidewire to separate from the catheter is greatest.

In a second exemplary embodiment, the guidewire channel in the flexible catheter tip is utilized as the sole guiding channel for the catheter. Such a construction provides a minimum catheter diameter and image artifact, but is somewhat less maneuverable and pushable than the first exemplary embodiment.

In a third exemplary embodiment, guidewire channels are provided in both the flexible catheter tip and on the flexible catheter body, but not on the housing. Such construction combines the best features of both the first and second embodiments, where the guidewire channel on the catheter body enhances maneuverability and pushability of the catheter, as the tendency for the guidewire to separate from the catheter is minimized, and minimizes the catheter diameter and image artifact as no additional structure on the housing is required.

BRIEF DESCRIPTION OF THE DRAWINGS

FIG. 1 illustrates a first embodiment of a catheter system constructed in accordance with the principles of the present invention.

FIG. 2 is a cross-sectional view of the distal end of the catheter system of FIG. 1.

FIG. 3 is a cross-sectional view taken along line 3—3 in FIG. 1.

FIG. 4 is a cross-sectional view taken along line 4—4 in FIG. 1.

FIG. 5 is a cross-sectional view taken along line 5—5 in FIG. 1.

FIG. 6 is a cross-sectional view taken along line 6—6 in FIG. 1.

FIG. 7 is a cross-sectional view of a distal tip of a second embodiment of the catheter system of the present invention.

FIG. 8 is a cross-sectional view taken along line 8—8 in FIG. 7.

FIG. 9 is a cross-sectional view taken along line 9—9 in FIG. 7.

FIG. 10 is a cross-sectional view taken along line 10—10 in FIG. 7.

FIG. 11 is a cross-sectional view of a distal tip of a third embodiment of the catheter system of the present invention.

FIG. 12 is a cross-sectional view taken along line 12—12 in FIG. 11.

FIG. 13 is a cross-sectional view taken along line 13—13 in FIG. 11.

FIG. 14 is a cross-sectional view taken along line 14—14 in FIG. 11.

FIG. 15 is a cross-sectional view taken along line 15—15 in FIG. 11.

FIG. 16 is perspective view of a catheter system of the type illustrated in FIG. 11, having open guidewire channels formed in the tip in the catheter body.

DESCRIPTION OF THE SPECIFIC EMBODIMENTS

The intravascular catheters of the present invention will include an elongate catheter body which is similar in construction to intravascular catheters of the type which are well known in the art. The catheter body will usually comprise a very flexible tube having proximal and distal ends and at least one lumen extending between said ends. The tube may be formed by extrusion of an organic polymer, typically a thermoplastic, such as nylon, polyurethane, polyethyleneterephthalate (PET), polyvinylchloride (PVC), polyethylene, and the like. The tubes so formed may be reinforced or unreinforced, with reinforcement being provided by metal wires, metal braided cables, or the like. The catheter body will typically have a length from about 60 to 150 cm and a diameter from about 3 to 11 French (F; 0.33 mm). For use in coronary applications, the catheter body will typically have a length from about 120 to 150 cm, and a diameter from about 3 to 6 French (F), while for peripheral applications, the catheter body will have a length from about 60 to 110 cm and a diameter from about 3 to 11 F.

The housing will be secured to or formed at the distal end of the catheter body. The housing may be open, i.e., include one or more apertures, gaps, or the like, which allow for unrestricted passage of materials or energy between the interior of the housing and the external environment, or may be closed. The housing may be formed separately or integrally with the structure of the catheter body. In either case, the housing will provide a more rigid structure than the catheter body. Usually, the housing will be very rigid, although a certain degree of flexibility may be desirable in certain applications.

The housing may be formed from metal, such as stainless steel, from a rigid plastic, or may be formed by reinforcement of the catheter body itself within the region intended as the housing. When intended for ultrasonic imaging, the housing will usually be open or formed from an ultrasonically transparent material. The housing will usually have a cylindrical diameter, having a diameter from about 3 to 11 F, more usually from about 3 to 8 F, although the geometry may vary as described in connection with the drawings hereinbelow.

A wide variety of internal components may be located within the housing in order to provide for various interventional and imaging capabilities, such as laser ablation, atherectomy, perfusion, therapeutic ultrasound, endoscopic imaging, ultrasonic imaging, and the like. The present invention will find its greatest use, however, with ultrasonic imaging systems including an ultrasonic element capable of generating and receiving an ultrasonic imaging signal. Mechanical components will also be provided for sweeping the ultrasonic element in a desired direction, typically a radial sweep as described in U.S. Pat. No. 4,794,931, the disclosure of which is incorporated herein by reference. The ultrasonic element may be directly rotated or the ultrasonic signal indirectly rotated using a rotatable mirror. Specific systems for providing ultrasonic imaging will be described in connection with the drawings hereinbelow.

A flexible catheter tip will be secured to or formed at the distal end of the catheter housing. The flexible tip may be substantially solid, substantially hollow, or have an intermediate construction, and will extend beyond the housing by a length of at least 0.5 cm, usually being from about 0.5 to 1.5 cm, more usually being from about 0.5 to 1.0 cm. The tip will be highly flexible, being more flexible than the catheter housing, and typically being as flexible or nearly flexible as the catheter body. The flexible tip may be formed from similar polymers as described in connection with the catheter body. The tip will usually be formed separately from the housing and the catheter body, but integral constructions where at least a portion of the flexible tip is formed continuously with the housing and/or the catheter body may also find use.

The primary guidewire channel of the present invention will be formed in the flexible tip and include a first port on the outer periphery of the tip adjacent the proximal end where the tip is attached to the housing. The guidewire channel extends through the tip to a second port formed at the distal end of the tip. By locating the first port on the periphery of the tip and the second port along the axial center of the tip, the guidewire may be readily received in the guidewire channel with a minimum tendency to seize as the catheter is advanced over the guidewire. The ability of the catheter to follow the guidewire is further enhanced by the flexibility of the tip which allows it to follow around even tight radii formed in tortuous regions of the vascular system.

In the preferred embodiments, the flexible tip has a conical geometry, where the first port is formed in the conical surface of the tip adjacent the base and the second port is formed in the conical apex. The conical tip is able to smoothly advance through the vascular system over the guidewire.

Referring now to FIGS. 1-6, a first catheter system 10 constructed in accordance with the principles of the present invention will be described. The catheter system 10 includes a catheter body 12, housing structure 14, and a flexible tip 16. The catheter body 12 includes a distal portion 18 having a central lumen 20 and guidewire lumen 22 formed therein. The remaining proximal portion of the catheter body 12 includes only central lumen 20. Proximal access to the guidewire lumen 22 is provided through peripheral port 24 formed at the proximal end of the distal region 18. As illustrated, the catheter body 12 and distal region 18 have a generally oval cross-section which provides an extended region for forming the guidewire lumen 22. In this way, a guidewire 26 may be received through the port 24 in a substantially parallel axial orientation.

Housing 14 includes cylindrical segments 30 and 32 and a separate tube 34 which is aligned with the guidewire lumen 22 and catheter body 12. Cylindrical segments 30 and 32, in turn, are aligned with the primary lumen 23, with segment 30 including an ultrasonic transducer 36 and segment 32 including a rotatable mirror 38. The rotatable mirror 38 is driven by a drive cable 40 which extends proximally through primary lumen 23 to a proximal housing 42, where it terminates in a drive coupling 44. A pair of wires 46 are also introduced to the catheter 10 through a port 47 in housing 42 and are ultimately connected with the transducer element 36. The wires 46 may be passed through a pair of small lumens 48 formed in the catheter wall (FIGS. 5 and 6), passing through the tube 34, and being connected to the transducer element 36. Housing 42 also includes a perfusion port 50 which is fluidly connected with the primary lumen 23. Additional ports in housing 42 and lumens in the catheter body 12 may be provided for other conventional purposes.

Distal tip 16 is a substantially solid elastomeric cone which is secured to the distal end of housing 14. Tip 16 includes the guidewire lumen 52 which extends from first port 54 which is aligned with the lumen of tube 34 to an apical port 56. In this way, wire lumens 52, 34, and 22 are connected in a substantially continuous path which allows guidewire 26 to enter through the apical port 56 and exit through the peripheral port 24 on the catheter body 12. The length of region 18 will typically be in the range from about 5 to 30 cm, more typically being in the range from about 10 to 20 cm.

Referring now to FIGS. 7-10, a second embodiment 60 of the catheter system of the present invention is illustrated. The embodiment 60 includes catheter body 62, housing 64, and a flexible catheter tip 66. The flexible tip 66 includes a guidewire lumen 68 which passes from an apical port 70 to a peripheral port 72. In contrast to the construction of FIGS. 1-6, the peripheral port 72 is formed on the outer conical surface of the tip 66 and allows guidewire 74 to extend to the exterior of the catheter 60, rather than passing through a guidewire lumen formed in the housing 64 or the catheter body 62. By forming the first port 72 flush with the conical wall at the base of the tip 66, smooth passage of the guidewire along the side of catheter 60 is enhanced. Provision of the second port at the apical tip of the catheter tip 66 similarly enhances the passage of the catheter along the guidewire through tortuous vascular paths.

The housing 64 is similar to housing 14 of FIGS. 1-6, except that axial struts 76 are provided in order to connect the first housing segment 78 with a second housing segment 80. The housing 64 includes an ultrasonic imaging element 82 and rotating mirror 84, where the mirror is driven by drive cable 86 which passes through a central lumen 88 of the catheter body 62.

Referring now to FIGS. 11-15, a third embodiment 100 of the catheter system of the present invention is illustrated. The catheter system 100 includes catheter body 102, catheter housing 104, and a flexible catheter tip 106. The construction of the flexible catheter tip 106 is substantially the same as that described for catheter tip 66 in FIGS. 7-10. Flexible tip 106 thus includes a first port 108 formed adjacent the base of the tip on its conical surface and a second port 110 formed at the apex of the flexible tip. The guidewire lumen 112 is thus able to receive guidewire 114 through the apical port 110 and release the guidewire adjacent to the outer surface of housing 104, as illustrated.

The catheter body 102 of catheter 100 includes a second guidewire lumen 116 formed parallel to the primary lumen 118. Guidewire lumen 116 includes a peripheral port 120 formed near the distal end of the catheter body and a second port 122 formed a preselected distance proximally to the first port. The preselected distance will usually be in the range from about 5 to 30 cm, more usually being in the range from about 10 to 20 cm. Location of the ports 120 and 122 on the periphery of the catheter allow entry and exit of the guidewire 114 with a minimal increase in the diameter of the catheter body 102. Moreover, the ability to route the guidewire 114 through the second guidewire lumen 116 enhances the maneuverability of the catheter 100 relative to catheter 60 of FIGS. 7-10. Moreover, passing of the guidewire 114 along the outside of housing 104 eliminates all interference with the internal components of the housing and, in the case of ultrasonic imaging catheters, minimizes the image artifact resulting from the presence of a guidewire lumen or channel.

Although the guidewire catheter 116 need only be formed within the distal end of catheter body 102, in some cases it may be convenient to continue the lumen throughout the remaining length of the catheter body. In that case, the lumen may be utilized for additional reinforcement, e.g., by placement of a stiffening wire, or for any other purpose. Alternatively, the lumen 116 may simply be blocked off, as illustrated by plug 124.

The ultrasonic imaging mechanism illustrated within housing 104 is substantially the same as those previously illustrated. An ultrasonic transducer element 130 is provided to project and receive ultrasonic energy from a rotating mirror 132. The mirror is driven by a drive cable 134 which extends proximally to a proximal housing (not illustrated). The housing 104, however, differs from earlier illustrations in that it is fully enclosed and not open to the surrounding environment.

Referring now to FIG. 16, a modification of the construction of the guidewire lumens of the present invention is illustrated. A catheter 130 which is constructed similarly to that illustrated in FIGS. 11-15, includes catheter body 132, housing 134, and flexible catheter tip 136. Instead of providing enclosed guidewire lumens, however, the flexible tip 136 in catheter body 132 include open guidewire channels 138 and 140, respectively. The open guidewire channel 138 in tip 136 extends from apical port 142 to peripheral port 144 to allow normal passage of a guidewire (not illustrated).

The open channel 138, however, allows the guidewire to be pulled from the channel without the need to pull the catheter over the entire length of the guidewire. Similarly, the open channel 140 in catheter body 142 allows the guidewire to be pulled from the catheter as it is removed from the patient.

Although the foregoing invention has been described in detail for purposes of clarity of understanding, it will be obvious that certain modifications may be practiced within the scope of the appended claims.

What is claimed is:

1. An imaging catheter comprising:
   a flexible catheter body having proximal and distal ends and a channel capable of receiving a movable guidewire extending between a first port on the periphery of the catheter body located a preselected distance proximally of the distal end and a second port on the periphery of the catheter body located adjacent the distal end;
   a substantially rigid housing secured to the distal end of the flexible catheter body, said housing having a substantially rigid radially-offset channel which is aligned with channel on the catheter body and capable of receiving the guidewire from the second port thereof;
   means within the housing for scanning an ultrasonic imaging signal across an environment surrounding the housing, wherein the means for scanning includes a fixed ultrasonic transducer and a rotatable mirror; and
   a flexible conical tip secured to a distal end of the housing and having a channel which is aligned with the channels on the catheter body and the housing and extending between a first port at the base of the tip and a second port at a conical apex of the tip, wherein the first port on the tip is capable of receiving the guidewire from the channel on the housing.

2. An imaging catheter as in claim 1, wherein the channels on the catheter body, housing, and flexible conical tip are substantially continuous.

3. An imaging catheter as in claim 1, wherein the distal end of the catheter body, the housing, and the base of the flexible conical tip all have non-circular peripheral geometries with a lateral extension to accommodate the guidewire channels.

4. An imaging catheter as in claim 1, wherein the preselected distance between the first and second ports on the catheter body is from about 5 to 30 cm.

5. An imaging catheter as in claim 1, wherein the guidewire channels are closed lumens.

6. An imaging catheter as in claim 1, wherein the guidewire channels are open to facilitate removal of the guidewire.

7. An imaging catheter as in claim 1, wherein the housing includes a distal segment and a proximal segment with an open gap therebetween, wherein the axial channel joins the two segments and the ultrasonic transducer is disposed in the distal segment and the rotatable mirror is disposed in the proximal segment.

* * * * *